(12) United States Patent
Gleich et al.

(10) Patent No.: US 11,592,341 B2
(45) Date of Patent: Feb. 28, 2023

(54) MAGNETIC MEASUREMENT DEVICE FOR MEASURING TEMPERATURE OR OTHER PROPERTY

(71) Applicant: KONINKLIJKE PHILIPS N.V., Eindhoven (NL)

(72) Inventors: Bernhard Gleich, Hamburg (DE); Juergen Erwin Rahmer, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 437 days.

(21) Appl. No.: 16/708,485

(22) Filed: Dec. 10, 2019

(65) Prior Publication Data

US 2020/0400509 A1 Dec. 24, 2020

(30) Foreign Application Priority Data

Jun. 20, 2019 (EP) .................................... 19181528

(51) Int. Cl.
| | |
|---|---|
| *G01K 7/00* | (2006.01) |
| *G01K 7/36* | (2006.01) |
| *G01K 1/26* | (2006.01) |
| *G01K 13/04* | (2006.01) |
| *A61B 5/0215* | (2006.01) |

(Continued)

(52) U.S. Cl.
CPC ............ *G01K 7/36* (2013.01); *A61B 1/00158* (2013.01); *A61B 5/0215* (2013.01); *A61B 5/02152* (2013.01); *A61B 5/05* (2013.01); *A61B 5/062* (2013.01); *A61B 5/6851* (2013.01); *A61B 5/6852* (2013.01); *A61B 34/20* (2016.02); *A61B 90/36* (2016.02); *A61B 90/39* (2016.02); *G01K 1/26* (2013.01); *G01K 13/04* (2013.01); *G01L 9/0001* (2013.01); *G01L 9/007* (2013.01); *A61B 5/02158* (2013.01); *A61B 2034/2051* (2016.02); *A61B 2034/2072* (2016.02); *A61B 2090/3958* (2016.02); *A61B 2090/3966* (2016.02); *A61B 2562/0223* (2013.01)

(58) Field of Classification Search
CPC combination set(s) only.
See application file for complete search history.

(56) References Cited

U.S. PATENT DOCUMENTS

| | | |
|---|---|---|
| 3,456,508 A | 7/1969 | Frische |
| 4,345,482 A | 8/1982 | Adolfsson |

(Continued)

FOREIGN PATENT DOCUMENTS

GB 626624 A 7/1949

*Primary Examiner* — Lisa M Caputo
*Assistant Examiner* — Nasir U. Ahmed
(74) *Attorney, Agent, or Firm* — Sherry Austin

(57) ABSTRACT

The invention relates to a measurement device 1 comprising a rotatable magnetic object 4 which can oscillate with a resonant frequency if excited by an external magnetic torque. The measurement device 1 is adapted such that the resonant frequency depends on the temperature or on another physical or chemical quantity like pressure, in order to allow for a wireless temperature measurement or measurement of the other physical or chemical quantity via an external magnetic field providing the external magnetic torque. This measurement device can be relatively small, can be read-out over a relatively larger distance and allows for a very accurate measurement.

20 Claims, 4 Drawing Sheets

(51) Int. Cl.

| | |
|---|---|
| *G01L 9/00* | (2006.01) |
| *A61B 34/20* | (2016.01) |
| *A61B 90/00* | (2016.01) |
| *A61B 5/06* | (2006.01) |
| *A61B 1/00* | (2006.01) |
| *A61B 5/05* | (2021.01) |
| *A61B 5/00* | (2006.01) |

(56) References Cited

U.S. PATENT DOCUMENTS

| | | | |
|---|---|---|---|
| 8,237,451 B2* | 8/2012 | Joy | A61B 5/0031 |
| | | | 324/633 |
| 10,215,825 B2* | 2/2019 | Zabow | G01R 33/5601 |
| 2004/0138555 A1 | 7/2004 | Krag et al. | |
| 2005/0174109 A1 | 8/2005 | Pullini | |
| 2006/0283007 A1 | 12/2006 | Cros et al. | |
| 2007/0236213 A1* | 10/2007 | Paden | A61B 3/16 |
| | | | 324/228 |
| 2010/0276501 A1* | 11/2010 | Yoshimura | A61B 5/055 |
| | | | 374/E7.039 |
| 2015/0126829 A1 | 5/2015 | Bernstein | |
| 2017/0234741 A1* | 8/2017 | Erickson | G01K 11/00 |
| | | | 374/188 |

* cited by examiner

MAGNETIC MEASUREMENT DEVICE FOR MEASURING TEMPERATURE OR OTHER PROPERTY

CROSS REFERENCE TO RELATED APPLICATIONS

This application claims priority to EP Application No. 19181528.1 filed Jun. 20, 2019, which is incorporated herein by reference.

FIELD OF THE INVENTION

The invention relates to a measurement device and a read-out system for measuring a temperature or another physical or chemical quantity like pressure. The invention also relates to a set of the measurement devices and to a measuring method and a computer program for measuring the temperature or the other physical or chemical quantity.

BACKGROUND OF THE INVENTION

Especially during interventional procedures it is often desired to accurately determine the temperature of, for instance, a certain tissue part of a subject like the temperature of a tumor, or to accurately consider the influence of temperature changes on a measurement of another physical or chemical quantity like pressure. However, in many cases the desired and often also required accuracy cannot be provided.

SUMMARY OF THE INVENTION

It is an object of the present invention to provide a measurement device and a read-out system which allow for an accurate determination of a temperature or of another physical or chemical quantity like pressure. It is a further object of the present invention to provide a set of the measurement devices and to provide a measuring method and a computer program for measuring the temperature or the other physical or chemical quantity. In a first aspect of the present invention a measurement device is presented, wherein the measurement device comprises:

a casing, a magnetic object being arranged within the casing such that it is rotatable out of an equilibrium orientation if an external magnetic torque is acting on the magnetic object, a restoring torque unit being adapted to provide a restoring torque to force the magnetic object back into the equilibrium orientation if an external magnetic torque has rotated the magnetic object out of the equilibrium orientation, in order to allow for a rotational oscillation of the magnetic object excited by the external magnetic torque with a resonant frequency, and a measurement element being adapted to modify the resonant frequency depending a) on the temperature and/or b) on the other physical or chemical quantity, wherein, if the measurement element is adapted to modify the resonant frequency depending on the other physical or chemical quantity, the measurement device comprises a compensation element which is adapted to modify the resonant frequency in a first frequency direction depending on a temperature change which is opposite to a second frequency direction in which the measurement device would modify the resonant frequency, depending on the temperature change, if the compensation element were not part of the measurement device.

Thus, for measuring the temperature it can be used that the measurement element modifies the resonant frequency depending on the temperature. It is hence possible to measure the temperature by determining the resonant frequency of the magnetic object, wherein a magnetic field can be generated, which provides a magnetic torque for rotating the magnetic object out of its equilibrium orientation and for thereby exciting a rotational oscillation of the magnetic object such that it oscillates with the resonant frequency, and wherein induction signals are generated that are caused by the rotational oscillation of the magnetic object. The temperature can then be determined based on the generated induction signals. In particular, the magnetic field can be generated with different excitation frequencies, wherein the resonant frequency can be determined as the excitation frequency at which the induction signal is optimized, wherein the determined resonant frequency can be used for determining the temperature based on known assignments between the resonant frequency and the temperature. This allows to determine the temperature very accurately.

Moreover, if the measurement element is adapted to modify the resonant frequency depending on the other physical or chemical quantity like pressure, also in this case the resonant frequency can be determined by using the magnetic field providing the magnetic torque for rotating the magnetic object of the measurement device and by using the generated induction signals, wherein the determined resonant frequency indicates the other physical or chemical quantity. Here known assignments between the resonant frequency and the other physical or chemical quantity can be used. Furthermore, since the measurement device comprises a compensation element which is adapted to modify the resonant frequency in a first frequency direction depending on a temperature change which is opposite to a second frequency direction in which the measurement device would modify the resonant frequency, depending on the temperature change, if the compensation element were not part of the measurement device, temperature induced shifts of the resonant frequency, which in this case are not desired, can be reduced or even eliminated. The first frequency direction is a direction towards higher or lower frequencies and the opposite second frequency direction is a direction towards lower or higher frequencies, respectively.

The measurement element is preferentially an additional element which is present in addition to the casing, the magnetic object and the restoring torque unit. It can be a single element or a combination of several sub elements. The measurement element can comprise, for instance, one or several magnetic materials which change their magnetization depending on the temperature and which can be arranged within the measurement device such that the resonant frequency changes with temperature, if the measurement element should be adapted to measure the temperature. However, these magnetic materials could also be chosen and arranged such that they compensate for an undesired temperature dependence of the resonant frequency of the measurement device, in order to make the resonant frequency of the measurement device independent of the temperature, if the measurement device should be used for measuring the other physical or chemical quantity.

It is noted that the term "external magnetic torque" refers to a magnetic torque caused by an external magnetic field providing unit being outside of the measurement device. Preferentially, the magnetic field providing unit is also outside of a subject, if the measurement device is arranged within the subject.

Preferentially the restoring torque unit comprises a further magnetic object for generating a magnetic field at the position of the magnetic object such that it provides the restoring torque and/or a torsional spring mechanism for providing the restoring torque. In an embodiment the magnetic object is attached to one end of a filament, wherein another end of the filament is attached to the casing, wherein the filament is adapted to prevent that the magnetic object touches the further magnetic object due to their magnetic attraction to allow the magnetic object to rotationally oscillate. The further magnetic object is preferentially stationarily attached to the casing. However, the further magnetic object can also be arranged within the casing such that it is rotationally oscillatable relative to the casing. In particular, the further magnetic object can be attached to one end of the filament, wherein another end of the filament can be attached to the casing. In an embodiment the further magnetic object can be rotatable around a virtual rotational axis centrally traversing the further magnetic object, wherein the further magnetic object is rotationally symmetric with respect to the virtual rotational axis. The magnetic object and/or the further magnetic object might be a sphere and/or magnetic cylinder. The virtual axes of the magnetic object and the further magnetic object are preferentially aligned with each other.

These techniques allow to provide a restoring torque and hence a rotational oscillation of the magnetic object such that the measurement device can be relatively small, the resonant frequency of the measurement device can be provided depending on the temperature or depending on the other physical or chemical quantity as desired and the construction of the measurement device can still be relatively simple.

In an embodiment the measurement device is adapted such that the further magnetic object is rotatable out of an equilibrium orientation if an external magnetic torque is acting on the magnetic object, wherein the restoring torque unit is adapted to also provide a restoring torque to force the further magnetic object back into the equilibrium orientation if an external magnetic torque has rotated the further magnetic object out of the equilibrium orientation, in order to allow for a rotational oscillation of the further magnetic object excited by the external magnetic torque, wherein the rotational oscillations of the magnetic object and the further magnetic object have the same resonant frequency and a phase difference of 180 degrees. This reduces, optimally even cancels, the torque on the casing. The restoring torque unit can use the magnetic object for providing the restoring force for the further magnetic object. In particular, in an embodiment the magnetic object forms a first magnetic dipole, the further magnetic object forms a second magnetic dipole, and the magnetic object and the further magnetic object are arranged such that in the equilibrium orientation the first and second magnetic dipoles point in opposite directions. In an embodiment the magnetic object and the further magnetic object are directly connected to each other via a torsion spring such that in this case the restoring torque unit comprises the torsion spring.

Preferentially the magnetic object and/or the further magnetic object is a permanent magnet. Moreover, the casing is preferentially cylindrical. If the casing is cylindrical, it can be relatively easily introduced into a tubular medical device like a guidewire.

Preferentially the measurement device is adapted to fulfill at least one condition of a list consisting of i) a Q factor of at least 100, ii) a dynamic dipole moment of at least 0.5 $\mu Am^2$, and iii) a resonant frequency of at least 100 Hz. It has been found that, if at least one of these conditions is fulfilled, the accuracy of determining the temperature or the other physical or chemical quantity can be further increased.

It is further preferred that the measurement device is radiopaque. This allows to visualize the measurement device also by using an x-ray imaging system like a computed tomography system, an x-ray fluoroscopy system, an x-ray C-arm system, et cetera. Preferentially the measurement element is adapted such that the strength of the generated magnetic field at the position of the magnetic object and/or the dipole moment of the magnetic object changes with a) the temperature and/or b) the other physical or chemical quantity. By changing the strength of the generated magnetic field at the position of the magnetic object and/or the dipole moment of the magnetic object with the temperature and/or with the other physical or chemical quantity, the resonant frequency can be changed depending the temperature and/or the other physical or chemical quantity in a technically relatively simple way.

In an embodiment the measurement element comprises magnetic material which influences the magnetic field generated by the further magnetic object, wherein the influence of the magnetic material depends on the temperature, in order to change the strength of the magnetic field at the position of the magnetic object, if the temperature changes. The magnetic material may be arranged adjacent to the further magnetic object. It may be adapted such that its magnetization decreases with increasing temperature. Moreover, it may be chosen and arranged such that its magnetization direction is opposite to the magnetization direction of the further magnetic object. However, it is also possible that the magnetic material is chosen and arranged such that its magnetization direction and the magnetization direction of the further magnetic object are the same. The magnetic material is preferentially a soft magnetic material. By using this magnetic material the resonant frequency can be modified depending on the temperature very accurately in a technically very relatively simple way without requiring much space.

In a preferred embodiment the measurement element is adapted such that the distance between the magnetic object and the further magnetic object changes, if the temperature changes and/or if the other physical or chemical quantity changes, in order to change the strength of the magnetic field at the position of the magnetic object. In an embodiment the other physical or chemical quantity is pressure, wherein the measurement element comprises a flexible part of a wall of the casing, wherein the magnetic object or the further magnetic object is attached to the flexible part such that external pressure acting against the flexible part from the outside of the casing leads to a change of the distance between the magnetic object and the further magnetic object.

In an embodiment the measurement element comprises a vapor bed on which the further magnetic object is located, wherein the size of the vapor bed and therefore the distance between the magnetic object and the further magnetic object changes with temperature. In a further embodiment the measurement element comprises a leverage construction via which the magnetic object is attached to the casing, wherein the leverage construction comprises material which changes its length depending on the temperature such that the distance between the magnetic object and the further magnetic object changes with temperature. Also these techniques allow for a very accurate provision of a temperature dependence of the resonant frequency.

In an embodiment the measurement element comprises magnetic material which is applied to the magnetic object and which influences the dipole moment of the magnetic object, wherein the influence of the magnetic material depends on the temperature, in order to change the dipole moment of the magnetic object, if the temperature changes.

Preferentially the compensation element comprises magnetic material which changes its magnetization and thereby the resonant frequency with temperature, wherein the magnetic material is chosen and arranged within the measurement device such that the direction of the modification of the resonant frequency is the first frequency direction. The compensating magnetic material is preferentially arranged adjacent to the magnet object and/or adjacent to the further magnet object. Also this allows to design the measurement device such that an unwanted temperature dependence can be significantly reduced or even eliminated in a technically relatively simple way and without requiring much space within the casing.

In a further aspect of the present invention a set of several measurement devices is presented, wherein each measurement device is adapted to have the resonant frequency in a respective frequency range, when the respective measurement device is used for the measurement, wherein the frequency ranges of different measurement devices do not overlap. By using this set of several measurement devices it is possible to carry out measurements of, for instance, the temperature and/or the other physical or chemical quantity simultaneously, wherein it is still possible to distinguish these measurements.

In an aspect of the present invention a read-out system for reading out the measurement device is presented, wherein the read-out system comprises:

an excitation and induction signal unit adapted to a) generate a magnetic field providing a magnetic torque for rotating the magnetic object of the measurement device out of its equilibrium orientation and for thereby exciting a rotational oscillation of the magnetic object such that it oscillates with the resonant frequency, and b) generate induction signals that are caused by the rotational oscillation of the magnetic object, a determination unit adapted to determine the temperature or the other physical or chemical quantity based on the generated induction signals.

In another aspect of the present invention a measuring method for carrying out a measurement by using the measurement device is presented, wherein the measuring method comprises:

generating a magnetic field providing a magnetic torque for rotating the magnetic object of the measurement device out of its equilibrium orientation and for thereby exciting a rotational oscillation of the magnetic object such that it oscillates with the resonant frequency, and generating induction signals that are caused by the rotational oscillation of the magnetic object, determining the temperature or the other physical or chemical quantity based on the generated induction signals.

In a further aspect of the present invention a computer program comprising program code means for causing a read-out system as defined by claim 13 to carry out the steps of the measuring method as defined in claim 14 is presented, when the computer program is run on a computer controlling the read-out system.

It shall be understood that the measurement device of claim 1, the set of measurement devices of claim 12, the read-out system of claim 13, the measuring method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
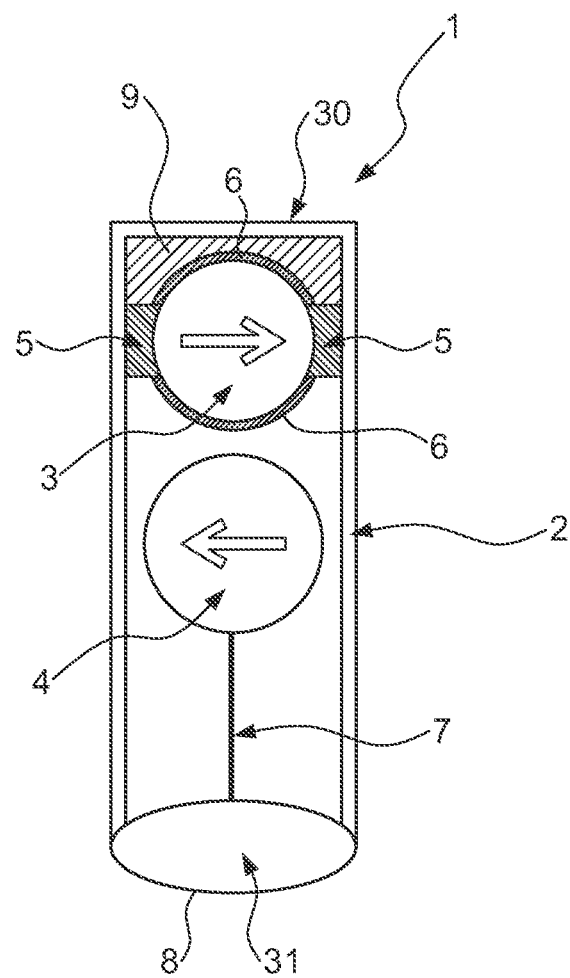
FIG. 1 shows schematically and exemplarily an embodiment of a measurement device for measuring pressure.

FIG. 1 shows schematically and exemplarily an embodiment of a measurement device. The measurement device 1 comprises a casing 2 and a magnetic object 4 being arranged within the casing 2 such that it is rotatable out of an equilibrium orientation if an external magnetic torque is acting on the magnetic object 4. The marker device 1 further comprises a restoring torque unit 3 being adapted to provide a restoring torque to force the magnetic object 4 back into the equilibrium orientation if an external magnetic force has rotated the magnetic object 4 out of the equilibrium orientation, in order to allow for a rotational oscillation of the magnetic object 4 excited by the external magnetic torque. In this embodiment the casing 2 is cylindrical and the magnetic object 4 is rotatable around a virtual rotational axis centrally traversing the magnetic object 4, wherein the magnetic object 4 is rotationally symmetric with respect to the virtual rotational axis. In particular, in this embodiment the magnetic object 4 is a magnetic sphere.

The restoring torque unit 3 comprises a further magnetic object 3 for providing the restoring torque. In particular, the magnetic object 4 is attached to one end of a filament 7, wherein another end of the filament 7 is attached to the casing 2. The filament 7 is adapted to prevent the magnetic object 4 from touching the further magnetic object 3 due to their magnetic attraction and to allow the magnetic object 4 to rotationally oscillate. In this embodiment the further magnetic object 3 is stationarily attached to the casing 2 by using glue 9.

The magnetic object 4 forms a first magnetic dipole, the further magnetic object 3 forms a second magnetic dipole and the magnetic object 4 and the further magnetic 3 are arranged such that in the equilibrium orientation the first and second dipoles point in opposite direction. Preferentially, the first magnetic object 4 and the second magnetic object 3 are permanent magnets, wherein in the equilibrium orientation a north pole of the magnetic object 4 faces a south pole of the further magnetic object 3 and vice versa.

The casing 2 is cylindrical, wherein the cylindrical casing 2 comprises two end surfaces 30, 31 and wherein the further magnetic object 3 is stationarily attached to a first end surface 30 and the end of the filament 7, which is opposite to the end attached to the magnetic object 4, is attached to a second end surface 31 of the cylindrical casing 2.

In this embodiment the second end surface 31 of the casing 2 is formed by a flexible part 8 of the wall of the casing 2, wherein the magnetic object 4 is attached to the flexible part 8 via the filament 7 such that external pressure acting against the flexible part 8 from the outside of the casing 2 leads to a change of the distance between the magnetic object 4 and the further magnetic object 3. Due to this distance change caused by the external pressure the strength of the magnetic field generated by the further magnetic object 3 at the position of the magnetic object 4 and hence the resonant frequency changes. Thus, the resonant frequency changes depending on the external pressure such that the measurement device 1 can be used for measuring the external pressure as the other physical quantity. The flexible part 8 of the wall of the casing 2 can therefore be regarded as being a measurement element which is adapted to modify the resonant frequency depending on the external pressure.

The measurement device 1 further comprises magnetic material 5, 6 arranged adjacent to the further magnetic object 3. This magnetic material 5, 6 influences the magnetic field generated by the further magnetic object 3, wherein the influence of the magnetic material 5, 6 depends on the temperature in order to change the strength of the magnetic field at the position of the magnetic object 4 and hence in order to change the resonant frequency, if the temperature changes. The magnetic material 5, 6 is adapted such that its magnetization decreases with increasing temperature. Moreover, the magnetic material 6 is adapted such that its magnetization direction is opposite to the magnetization direction of the further magnetic object 3 and the magnetic material 5 is adapted such that its magnetization direction and the magnetization direction of the further magnetic object 3 are the same. The magnetic materials 5, 6, which are soft magnetic materials, therefore influence the resonant frequency depending on the temperature in opposite frequency directions, i.e. one of these magnetic materials leads to a change towards higher frequencies depending on an increasing temperature and the other of these magnetic materials leads to a change towards lower frequencies with increasing temperature.

In this embodiment the measurement device should be used for measuring the pressure such that the resonant frequency should not depend on the temperature. However, for instance, the flexible part 8 of the wall of the casing, which might be formed by a membrane, might have a temperature-depended flexibility such that the resonant frequency might generally depend also on the temperature. Also further parts of the measurement device might depend on the temperature, wherein this dependence might also influence the resonant frequency. In order to compensate this unwanted temperature dependent frequency shift, the magnetic materials 5, 6 can be tailored such that they provide the same frequency shift in an opposite frequency direction depending on a temperature change. In particular, the magnetic materials 5, 6 can be chosen and arranged such that any temperature dependence of the resonant frequency of the measurement device 1 is eliminated. It is also possible that only one of the magnetic materials, i.e. only a magnetic material decreasing the resonant frequency with increasing temperature or only a material increasing the resonant frequency with increasing temperature, is used for reducing or even eliminating the temperature dependence of the resonant frequency of the measurement device 1.

In a further embodiment the second end surface 31 does not comprise the flexible part 8, but is also rigid, and soft magnetic material is applied to increase the temperature dependence of the resonant frequency, in order to use the measurement device for temperature measurements. Also in this embodiment only one of the described magnetic materials shifting the resonant frequency in opposite directions depending on a temperature change might be used. In particular, in this embodiment preferentially only the magnetic material 6 is used, which has a magnetization direction which is aligned with the magnetization direction of the further magnetic object 3.

If the measurement device is used for measuring the temperature, the magnetic materials 5, 6 can be regarded as being measurement elements being adapted to modify the resonant frequency depending on the temperature. If the measurement device is used for measuring the pressure, the flexible part 8 of the wall of the casing 2 is regarded as being a measurement element being adapted to modify the resonant frequency depending on the pressure and the magnetic material 6 is regarded as being a compensation element which is adapted to modify the resonant frequency depending on the temperature in a first frequency direction depending on a temperature change which is opposite to a second frequency direction in which the measurement device would modify the resonant frequency, depending on the temperature change, if the compensation element 6 were not part of the measurement device.

Figure 2:
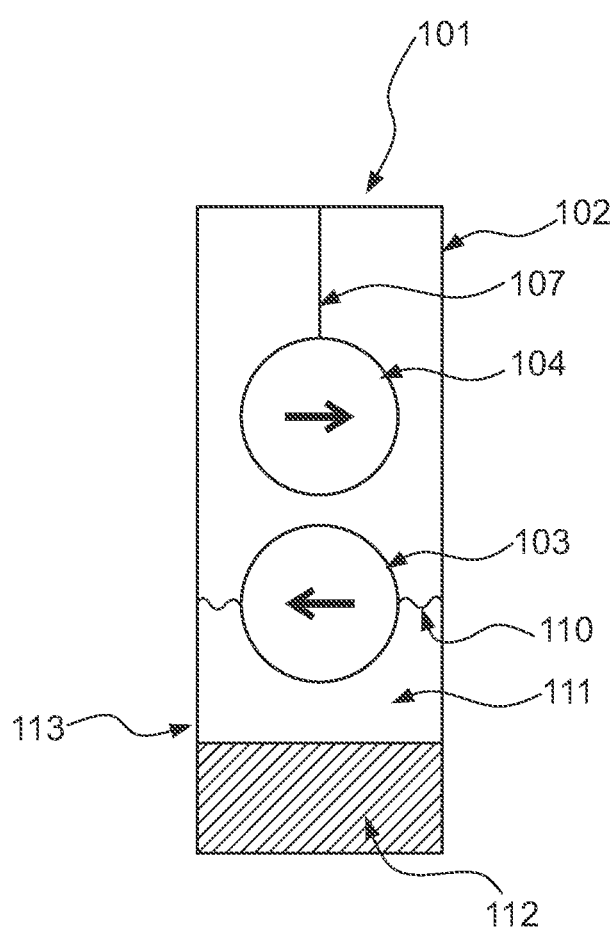
FIG. 2 shows schematically and exemplarily a further embodiment of a measurement device for measuring a temperature.

FIG. 2 shows schematically and exemplarily another embodiment of a measurement device. The measurement device 101 is adapted to measure the temperature, wherein in this embodiment the measurement element comprises a vapor bed 113 on which the further magnetic object 103 is located, wherein the size of the vapor bed 113 and therefore the distance between the rotating magnetic object 104 and the further magnetic object 103 changes with temperature. Also in this embodiment the measurement device 101 comprises a casing 102 and the magnetic object 104 is arranged within the casing 102 such that it is rotatable out of an equilibrium orientation if an external magnetic torque is acting on the magnetic object 104. Moreover, also this embodiment the magnetic object 104 is attached to an end surface of the casing 102 via a filament 107. The restoring torque is provided by the further magnetic object 103, wherein similar to the embodiment described above with reference to FIG. 1, in the equilibrium orientation of the rotatable magnetic object 104 the magnetic dipoles of the magnetic object 104 and the further magnetic object 103 point in opposite directions. The vapor bed 113 comprises a membrane 110, vapor 111 and liquid 112 which might be adsorbed to solid material. The vapor volume and hence the distance between the magnetic object 104 and further magnetic object 103 changes if the temperature changes, thereby modifying the resonant frequency with changing temperature.

Figure 3:
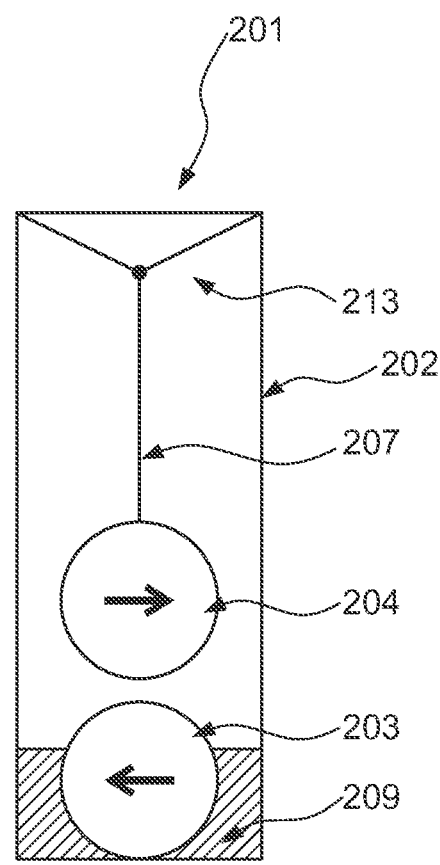
FIG. 3 shows schematically and exemplarily a further embodiment of a measurement device for measuring a temperature.

FIG. 3 shows schematically and exemplarily a further embodiment of the measurement device. The measurement device 201 also comprises a casing 202, a magnetic object 204 being arranged within the casing 202 such that it is rotatable out of an equilibrium orientation if an external magnetic torque is acting on the magnetic object 204 and a restoring torque unit 203 comprising a further magnetic object 203. Also in this embodiment in the equilibrium orientation of the magnetic object 204 the magnetic dipoles of the magnetic object 204 and of the further magnetic object 203 point in opposite directions. The further magnetic object 203 is attached to an end surface of the casing 202 by using, for instance, glue 209. In this embodiment the measurement element being adapted to modify the resonant frequency depending on the temperature comprises a leverage construction 213 via which the magnetic object 204 is attached to the casing 202, wherein the leverage construction 213 comprises material which changes its length depending on the temperature such that the distance between the magnetic object 204 and the further magnetic object 203 and hence the resonant frequency changes with temperature.

Figure 4:
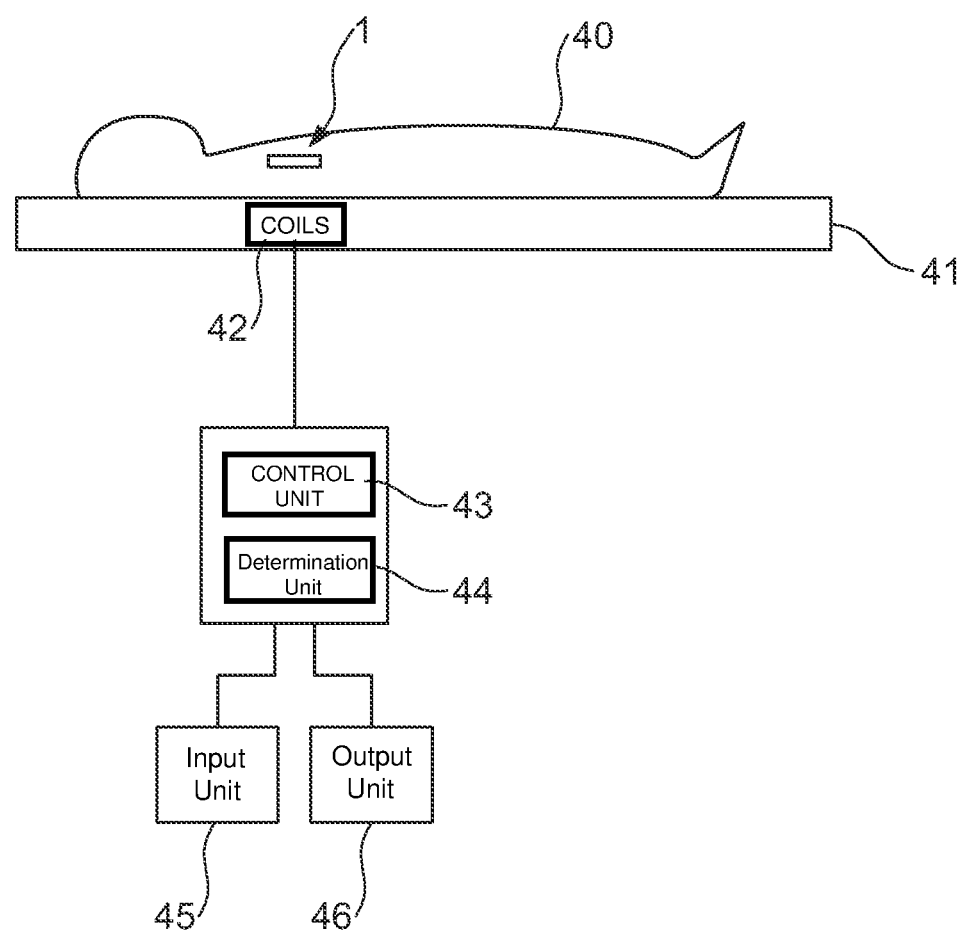
FIG. 4 shows schematically and exemplarily an embodiment of a read-out system for reading out the measurement device.

FIG. 4 shows schematically and exemplarily an embodiment of a read-out system for reading out the measurement device. In this example a subject 40 is located on a support means 41 like a patient table, wherein coils 42 are integrated in the support means 41. The coils 42 can also be arranged in another way close to the subject 40. For instance, they can be integrated in a mat which may be placed on the support means 41. A measurement device 1 has been introduced into the subject 40, in order to measure pressure within the subject 40.

The coils 42 are adapted to a) generate a magnetic field providing a magnetic torque for rotating the magnetic object 4 of the measurement device 1 out of its equilibrium orientation and for thereby exciting a rotational oscillation of the magnetic object 4 such that it oscillates with the resonant frequency, and b) generate induction signals that are caused by the rotational oscillation of the magnetic object 4. The read-out system further comprises a control unit 43 being configured to control the coils 42 by providing and controlling the current for the coils 42 such that the desired magnetic field is generated and to generate digital induction signals indicative of the induction influences on the currents within the coils caused by the rotational oscillation of the magnetic object 4 of the measurement device 1. The coils 42 and the control unit 43 magnetically excite the measurement device 1 and generate an induction signal such that the coils 42 and the control unit 43 can be regarded as forming an excitation and induction signal unit 42, 43.

Although in this embodiment the same coils are used for generating the magnetic field and for generating the induction signals, in other embodiments it is also possible that a) first coils are used for generating the magnetic field providing the magnetic torque for rotating the magnetic object 4 of the measurement device 1 out of its equilibrium orientation and for thereby exciting the rotational oscillation of the magnetic object 3 and b) second coils are used for generating the induction signals, wherein the first and second coils are separated.

The read-out system further comprises a determination unit 44 being adapted to determine the temperature or the other physical or chemical quantity based on the generated induction signals. In particular, the read-out system is adapted to provide the magnetic field with different excitation frequencies, wherein the excitation frequency is determined at which the generated induction signals indicate maximum induction and wherein this determined excitation frequency is regarded as being the resonant frequency. Moreover, the determination unit 44 can comprise predetermined assignments between a) resonant frequencies and b) temperatures or other physical or chemical quantities, respectively, and use the assignments together with the currently measured resonant frequency for determining the temperature or the other physical or chemical quantity, respectively.

The read-out system further comprises an input unit 45 like a keyboard, a computer mouse, touch pad, et cetera and an output unit 46 like a monitor for outputting the determined temperature or other physical or chemical quantity, respectively.

Figure 5:
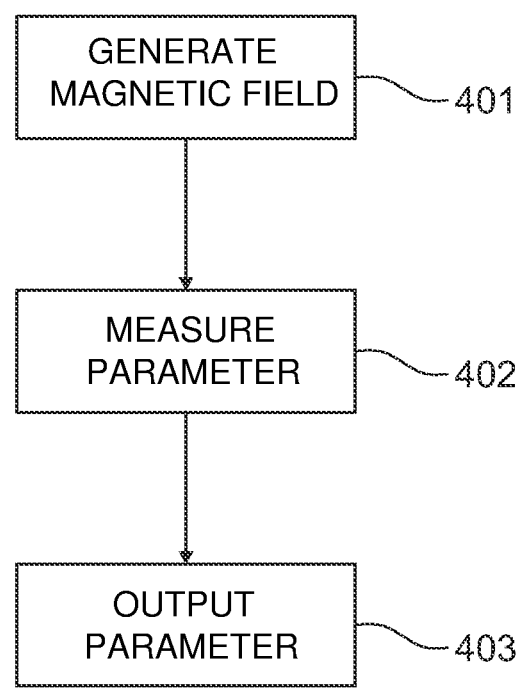
FIG. 5 shows a flowchart exemplarily illustrating an embodiment of a measuring method for measuring a temperature or another physical or chemical quantity.

In the following an embodiment of a measuring method for carrying out a measurement by using the measurement device 1 will exemplarily described with reference to a flowchart shown in FIG. 5.

In step 401 a magnetic field is generated which provides a magnetic torque for rotating the magnetic object 4 of the measurement device 1 within the subject 40 out of its equilibrium orientation and for thereby exciting a rotational oscillation of the magnetic object 4 such that it oscillates with the resonant frequency of the rotational oscillation of the magnetic object 4. Moreover, in step 401 induction signals are generated, which are caused by the rotational oscillation of the magnetic object 4. In particular, the magnetic field is generated with different excitation frequencies including the resonant frequency. Thus, although the resonant frequency is initially unknown and should be determined, it is known in which frequency range the resonant frequency will likely be present, wherein the magnetic field is generated with excitation frequencies covering the known frequency range in which the resonant frequency is to be expected. In step 402 the temperature or the other physical or chemical quantity, respectively, is determined based on the generated induction signals and in step 403 the determined temperature or other physical or chemical quantity, respectively, is outputted.

Steps 401 to 403 might be carried out in a loop such that substantially continuously the measurement is carried out and outputted to, for instance, a physician performing, for example, as surgical procedure, until the measurement is aborted. The measurement might be aborted, after a desired stop of the measurement has been indicated to the read-out system via the input unit 45.

The measurement device can especially be used in thermal ablation procedures, in order to control the thermal energy applied to a subject depending on the measured temperature. The measurement device has preferentially a sub-millimeter size and can be placed in or at the tissue to be ablated, in order to monitor the temperature of the tissue during the ablation procedure. The measurement device provides a wireless solution for measuring the temperature or the other physical or chemical quantity like the pressure such that the measurement device may be delivered, for instance, via the blood stream to a desired location within the subject. The measurement device can be placed, for instance, at or within a tumor for monitoring the temperature during a tumor ablation procedure. The measurement device is not only very small, i.e. of sub-millimeter size, but also highly sensitive and very accurate, wherein the measurement device can be probed remotely by a coil system, for instance, as described above.

The magnetic material to be used for modifying the temperature dependence of the measurement device as desired like the magnetic materials 5, 6 described above with reference to FIG. 1 is preferentially a low Curie temperature material, wherein this magnetic material might also be applied to the embodiments described above with reference to FIGS. 2 and 3 for tailoring the temperature dependence of the resonant frequency as desired. The casing of the measurement device can be, for instance, a metal or polymer casing. Moreover, within the casing gas can be present or it can also contain a vacuum.

The measurement device preferentially comprises two magnetic objects that can rotate relative to each other, wherein in an embodiment one of the two magnetic objects is fixed to the casing, for instance, by glue and the other of the magnetic objects is suspended by a filament like a fine wire or a thread. The oscillation frequency depends on the magnetic strength at the oscillating magnetic object, which is preferentially a sphere, and therefore on the distance between the magnetic objects. Thus, by translating a physical or chemical quantity that shall be measured into a distance change by a suitable measurement structure, a shift of the resonant frequency can be obtained and used for measuring the physical or chemical quantity. In case of a pressure measurement, the measurement structure, i.e. the measurement element, may be simply a membrane. In case of using the device for measuring the temperature, a measurement element is used, which is adapted to increase the natural temperature dependence of the resonant frequency, which is generally not very high. For instance, while the thermal expansion of the casing might increase the distance between the magnetic objects, the thermal expansion of the filament reduces this distance. The overall change in resonant frequency is hence not very high depending on a temperature change. As a measurement element a filament could be used having a negative length change with increasing temperature, in order to also increase the distance between the two magnetic objects with increasing temperature. Such a filament could be or comprise a carbon fiber or stretched polymer fibers. However, preferentially the measurement element is an additional element like the above described magnetic material. The magnetic material preferentially has a Curie temperature only slightly above the maximum operation temperature of the measurement device. The magnetic material can be applied to many different positions within the measurement device, but preferentially the magnetic material is positioned near the further magnetic object which is preferentially fixed. Typically, the magnetic material loses magnetization with increasing temperature. However, depending on the position where this low Curie temperature material resides, the effect on the frequency is either positive or negative, i.e. the frequency is either shifted towards higher frequencies or toward lower frequencies with increasing temperature. In FIG. 1 the magnetic material 6 is a soft magnetic material which magnetizes in opposite direction compared to the further magnetic object 3 and thus always reduces the field strength at the position of the rotating magnetic object 4. The magnetic material 5 however has the same magnetization direction as the further magnetic object 3 and thus always increases the field strength and hence the resonant frequency decreases with increasing temperature. By using the magnetic material it is hence possible to tailor the direction of the temperature dependence of the resonant frequency and the strength of this temperature dependence as desired. The magnetic material can therefore be used to compensate a wide range of unwanted temperature drifts. The magnetic material might be an iron nickel alloy, wherein the Curie temperature is adjustable by the composition of this alloy. However, also other low Curie materials can be used.

The magnetic material can have, for instance, a Curie temperature being 100 K or less above the maximum operation temperature of the measurement device. In an embodiment the Curie temperature is 10 K above the maximum operation temperature of the measurement device. The magnetic material might also be a combination of several magnetic materials, which might be called sub magnetic material, having different Curie temperatures. If the magnetic material is a combination of several sub magnetic materials, one or several of the sub magnetic materials might also have a Curie temperature below the maximum operation temperature.

The maximum operation temperature depends on the application for which the measurement device should be used. It might be equal to or smaller than 50° C. or equal to or smaller than 100° C. In an embodiment the measurement device is adapted to be just used for measuring the body temperature. The maximum operation temperature might then be 50° C. In case of ablation monitoring the maximum operation temperature might be 100° C. If the measurement device is used in non-medical applications, the maximum operation temperature can be even higher.

The measurement device can also comprise other measurement elements for providing a high sensitivity of the resonant frequency with respect to temperature changes. For instance, the vapor pressure of liquid can be used to actuate a distance change between the magnetic objects, for instance, as described above with reference to FIG. 2. It is also possible that the thermal expansion of material is used together with a leverage construction for generating a high distance change with changing temperature, for instance, as described above with reference to FIG. 3.

During the measurement several measurement devices might be used simultaneously, wherein these several measurement devices are adapted to have a respective resonant frequency in a respective frequency range, when the respective measurement device is used for the measurement, and wherein the frequency ranges of different measurement devices do not overlap. This allows the read-out system to distinguish the different measurement devices based on the respective resonant frequency and to determine for each respective measurement device the respective temperature or other physical or chemical property, respectively.

If the measurement device is used for determining the temperature, the measurement element like the above mentioned soft magnetic material is preferentially chosen and arranged such that the change of the resonant frequency depending on the temperature is larger or equal 10 Hz/K and further preferred larger or equal to 100 Hz/K. If the measurement device is adapted to measure the other physical or chemical property, the measurement element is preferentially chosen and arranged such that the dependence of the resonant frequency on the temperature is equal to or smaller than 1 Hz/K. And further preferred smaller than 0.1 Hz/K.

Although above certain embodiments of measurement devices are described, also other measurement devices can be used, which comprise the casing, the rotatable magnetic object, the restoring torque unit providing a restoring torque to force the magnetic object back into an equilibrium orientation and a measurement element being adapted to modify the resonant frequency depending on the temperature and/or on the other physical or chemical quantity, wherein, if the measurement element is adapted to modify the resonant frequency depending on the other physical or chemical quantity, the measurement device comprises a compensation element which is adapted to modify the resonant frequency depending on the temperature in a first frequency direction depending on a temperature change which is opposite to a second frequency direction in which the measurement device would modify the resonant frequency, depending on the temperature change, if the compensation element were not part of the measurement device. For instance, in an embodiment the flexible part 8 of the casing 2 shown in FIG. 1 is rigid and the casing 2 can partly be filled with a liquid preferentially adsorbed to solid material such that vapor is present within the casing, wherein in this example the casing has some flexibility such that it, for instance, changes its length and/or can be curved, wherein this flexibility together with the temperature dependence of the vapor within the casing can lead to a change of the distance between the two magnetic objects within the casing and hence to a shift of the resonant frequency depending on the temperature. It is also possible that in FIG. 3 the leverage structure comprises more arcs than the one arc 213 shown in this figure in order to increase the temperature sensitivity. Furthermore, it is also possible that the restoring torque unit comprises, in addition to the further magnetic object or as an alternative, a torsion spring mechanism for providing the restoring torque. For instance, instead of the filament 7 shown in FIG. 1 a torsion spring can be used. It is also possible that two torsion springs are used, wherein each torsion spring connects the rotating magnetic object 4 with a respective one of the opposing and surfaces 30, 31. Moreover, it is also possible that in a measurement device the measurement element comprises magnetic material which is applied to the magnetic object and which influences the dipole moment of the magnetic object, wherein the influence of the magnetic material depends on the temperature, in order to change the dipole moment of the magnetic object, if the temperature changes. Thus, magnetic material, which changes its magnetization depending on the temperature, can also be applied to the rotating magnetic object.

Although in an above described embodiment the measurement device is adapted to measure the pressure as the other physical or chemical quantity, in other embodiments the measurement device can also be adapted to measure another physical or chemical quantity. This can be achieved, for instance, by constructing the measurement device such that a change of the desired physical or chemical quantity leads to a change of the distance between the magnetic object and the further magnetic object or, more generally, in a change of the restoring torque provided by the restoring torque unit.

One example of a further chemical parameter to measure would be to use a membrane made from a material (e.g. natural rubber) that changes mechanical properties in the presence of an organic solvent in the environment. If the casing has some sort of hole i.e. no pressure is measured, then this device would give the recording of organic solvents in the environment.

The generation of the magnetic field which provides a magnetic torque for rotating the magnetic object of the measurement device out of its equilibrium orientation and for thereby exciting a rotational oscillation of the magnetic object such that it oscillates with the resonant frequency can be implemented in many different ways. For instance, the excitation can use individual single pulses of a magnetic field, wherein between the pulses the frequency and phase of the induced signal can be measured. From this, the timing of the next short pulse can be computed such that it increases the oscillation amplitude of the magnetic object. As an alternative, the single pulse can be replaced with a pulse train of few pulses with positive and negative amplitudes. This short pulse train still covers a relative broad potential excitation spectrum, the center of which is designed to lay approximately at the expected resonant frequency. The timing of the pulse train is again adjusted so that it increases the oscillation amplitude of the magnetic object. The frequency of the resulting optimized induction signal can be regarded as being the resonant frequency.

In an embodiment the read-out system can also be adapted to generate induction signals that depend on the spatial position and optionally also on the orientation of the measurement device, wherein the determination unit can be adapted to determine the position and optionally also the orientation of the measurement device based on the generated induction signals. In particular, spatial sensitivity profiles of the individual coils can be used for determining the position and optionally also the orientation of the measurement device.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of the temperature or of the other physical or chemical quantity, the control of the excitation of the one or several measurement devices by controlling the current within the coils, et cetera, performed by one or several units or devices can be performed by any other number of units or devices. These procedures and/or the control of the read-out system in accordance with the measuring method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a measurement device comprising a rotatable magnetic object which can oscillate with a resonant frequency if excited by an external magnetic torque. The measurement device is adapted such that the resonant frequency depends on the temperature or on another physical or chemical quantity like pressure, in order to allow for a wireless temperature measurement or measurement of the other physical or chemical quantity via an external magnetic field providing the external magnetic torque. This measurement device can be relatively small, can be read-out over a relatively larger distance and allows for a very accurate measurement.

The invention claimed is:
1. A measurement device, comprising:
   a casing,
   a magnetic object, wherein the magnetic object is arranged within the casing such that it is rotatable out of an equilibrium orientation when an external magnetic torque is acting on the magnetic object,
   a restoring torque unit, wherein the restoring torque unit is configured to provide a restoring torque to force the magnetic object back into the equilibrium orientation when the external magnetic torque has rotated the magnetic object out of the equilibrium orientation, in order to allow for a rotational oscillation of the magnetic object, which is excited by the external magnetic torque, wherein the rotational oscillation has a resonant frequency, and
   a measurement element, wherein the measurement element is configured to modify the resonant frequency depending on a) the temperature and/or b) another physical or chemical quantity, wherein the chemical quantity indicates whether an organic solvent is present.

2. The measurement device of claim 1, wherein the restoring torque unit comprises a further magnetic object, wherein the further magnetic object is configured to generate a magnetic field at the position of the magnetic object such that it provides the restoring torque, and/or a torsional spring mechanism which is configured to provide the restoring torque.

3. The measurement device of claim 2, wherein the measurement element is adapted such that the strength of the generated magnetic field at the position of the magnetic object and/or the dipole moment of the magnetic object, changes with a) the temperature and/or b) the other physical or chemical quantity.

4. The measurement device of claim 3, comprising the further magnetic object, wherein the measurement element comprises magnetic material which influences the magnetic field generated by the further magnetic object, wherein the influence of the magnetic material depends on the temperature, in order to change the strength of the magnetic field at the position of the magnetic object when the temperature changes.

5. The measurement device of claim 4, wherein the magnetic material is arranged adjacent to the further magnetic object.

6. The measurement device of claim 4, wherein the magnetic material is adapted such that its magnetization decreases with increasing temperature.

7. The measurement device of claim 3, wherein the measurement element is adapted such that the distance between the magnetic object and the further magnetic object changes when the temperature changes and/or when the other physical or chemical quantity changes, in order to change the strength of the magnetic field at the position of the magnetic object.

8. The measurement device of claim 3, wherein the measurement element comprises magnetic material which is applied to the magnetic object and which influences the dipole moment of the magnetic object, wherein the influence of the magnetic material depends on the temperature, in order to change the dipole moment of the magnetic object when the temperature changes.

9. The measurement device of claim 2, wherein the restoring torque unit comprises the further magnetic object, wherein in the equilibrium orientation one of: (1) a north pole of the magnetic object faces a south pole of the further magnetic object; and (2) a south pole of the magnetic object faces a north pole of the further magnetic object.

10. A set of several measurement devices as defined in claim 1, wherein each measurement device is adapted to have the resonant frequency in a respective frequency range, when the respective measurement device is used for the measurement, wherein the frequency ranges of different measurement devices do not overlap.

11. A read-out system for reading out the measurement device of claim 1, wherein the read-out system comprises:
an excitation and induction signal unit adapted to a) generate a magnetic field providing the magnetic torque for rotating the magnetic object of the measurement device out of its equilibrium orientation and for thereby exciting a rotational oscillation of the magnetic object such that it oscillates with the resonant frequency, and b) generate induction signals that are caused by the rotational oscillation of the magnetic object,
a determination unit adapted to determine the temperature and/or the other physical or chemical quantity based on the generated induction signals.

12. A measuring method for carrying out a measurement by using the measurement device of claim 1, wherein the measuring method comprises:
generating a magnetic field providing the magnetic torque for rotating the magnetic object of the measurement device out of its equilibrium orientation and for thereby exciting a rotational oscillation of the magnetic object such that it oscillates with the resonant frequency, and generating induction signals that are caused by the rotational oscillation of the magnetic object,
determining the temperature and/or the other physical or chemical quantity based on the generated induction signals.

13. A non-transitory computer readable medium configured to store a computer program comprising machine executable instructions for causing a read-out system to carry out the steps of the measuring method of claim 12, when the computer program is run on a computer controlling the read-out system, wherein the read out system includes:
an excitation and induction signal unit adapted to:
a) generate a magnetic field providing the magnetic torque for rotating the magnetic object of the measurement device out of its equilibrium orientation and for thereby exciting a rotational oscillation of the magnetic object such that it oscillates with the resonant frequency, and
b) generate induction signals that are caused by the rotational oscillation of the magnetic object; and
a determination unit adapted to determine the temperature and/or the other physical or chemical quantity based on the generated induction signals.

14. The measurement device of claim 1, wherein the measurement element is configured to modify the resonant frequency depending on the other physical or chemical quantity, wherein one of more components of the measurement device modify the resonant frequency in a first direction in response to a change in temperature, and wherein the measurement device further comprises a compensation element which is configured to modify the resonant frequency in a second frequency direction which is opposite to the first frequency direction in response to the change in temperature.

15. The measurement device of claim 14, wherein the compensation element comprises magnetic material which changes its magnetization and thereby the resonant frequency with temperature, wherein the magnetic material is chosen and arranged within the measurement device such that the direction of the modification of the resonant frequency is in the second frequency direction.

16. The measurement device of claim 15, wherein the magnetic material is arranged adjacent to the magnet object.

17. The measurement device of claim 15, wherein the magnetic material is arranged adjacent to the further magnet object.

18. The measurement device of claim 14, wherein the one or more components of the measurement device which modify the resonant frequency in the first direction in response to the change in temperature includes the measurement element.

19. The measurement device of claim 1, wherein the measurement element is configured to modify the resonant frequency depending on the other physical or chemical quantity, wherein the other physical or chemical quantity comprises a presence of an organic solvent.

20. The measurement device of claim 1, wherein the restoring torque unit comprises a further magnetic object, wherein in the equilibrium orientation a first pole of the magnetic object faces an opposite pole of the further magnetic object.

* * * * *